(12) United States Patent
Bates et al.

(10) Patent No.: US 11,269,755 B2
(45) Date of Patent: Mar. 8, 2022

(54) SOCIAL MEDIA MONITORING SYSTEM AND METHOD

(71) Applicant: HUMANITY X TECHNOLOGIES, Phoenix, AZ (US)

(72) Inventors: Jordan T. Bates, Scottsdale, AZ (US); Bin Hong Lee, Mountain View, CA (US); Kacie McCollum, Phoenix, AZ (US); Pat Pataranutaporn, Cambridge, MA (US); Ram N. Polur, Phoenix, AZ (US)

(73) Assignee: Humanity X Technologies, Phoenix, AZ (US)

( * ) Notice: Subject to any disclaimer, the term of this patent is extended or adjusted under 35 U.S.C. 154(b) by 0 days.

(21) Appl. No.: 16/358,685

(22) Filed: Mar. 19, 2019

(65) Prior Publication Data

US 2019/0286540 A1    Sep. 19, 2019

Related U.S. Application Data

(60) Provisional application No. 62/644,719, filed on Mar. 19, 2018.

(51) Int. Cl.
| | | |
|---|---|---|
| G06F 11/34 | (2006.01) | |
| G16H 50/20 | (2018.01) | |
| G06K 9/62 | (2006.01) | |
| G06N 20/00 | (2019.01) | |
| G06Q 50/00 | (2012.01) | |

(52) U.S. Cl.
CPC ........ G06F 11/3438 (2013.01); G06K 9/6218 (2013.01); G06K 9/6267 (2013.01); G06N 20/00 (2019.01); G06Q 50/01 (2013.01); G16H 50/20 (2018.01)

(58) Field of Classification Search
None
See application file for complete search history.

(56) References Cited

U.S. PATENT DOCUMENTS

| | | |
|---|---|---|
| 7,788,087 B2 | 8/2010 | Corston-Oliver et al. |
| 8,165,974 B2 | 4/2012 | Privault et al. |
| 8,977,620 B1 | 3/2015 | Buryak et al. |
| 9,043,329 B1 | 5/2015 | Patton et al. |
| 9,077,782 B2 | 7/2015 | Harris et al. |
| 9,111,218 B1 | 8/2015 | Lewis et al. |
| 9,213,997 B2 | 12/2015 | Chatterjee et al. |
| 9,430,738 B1 | 8/2016 | Hui et al. |
| 9,460,163 B1 | 10/2016 | Toal et al. |
| 9,471,883 B2 | 10/2016 | Chatterjee et al. |
| 2012/0042020 A1 | 2/2012 | Kolari et al. |
| 2013/0198204 A1 | 8/2013 | Williams et al. |

(Continued)

FOREIGN PATENT DOCUMENTS

| | | |
|---|---|---|
| WO | 2017091214 A1 | 6/2017 |
| WO | 2017147301 A1 | 8/2017 |

*Primary Examiner* — Scott B Christensen
(74) *Attorney, Agent, or Firm* — Skaar Ulbrich Macari, P.A.

(57) ABSTRACT

Systems and methods for monitoring one or more social media accounts of one or more users to process potentially relevant or important activity. The system can employ automated filtering methods to select from all social media activity the data that is most likely to be relevant for review. The systems and methods can be employed with user accounts or services not associated with social media.

20 Claims, 13 Drawing Sheets

(56) References Cited

U.S. PATENT DOCUMENTS

| | | |
|---|---|---|
| 2013/0238599 A1 | 9/2013 | Burris |
| 2013/0254170 A1* | 9/2013 | Erhart .................... H04L 67/22 |
| | | 707/692 |
| 2013/0262320 A1* | 10/2013 | Makanawala ........ G06Q 30/016 |
| | | 705/304 |
| 2014/0040371 A1 | 2/2014 | Gurevich et al. |
| 2014/0324713 A1* | 10/2014 | Gordon .................. G06Q 10/10 |
| | | 705/311 |
| 2015/0088491 A1 | 3/2015 | Fume et al. |
| 2017/0061248 A1* | 3/2017 | Ryan, Jr. ................ G06K 9/627 |
| 2017/0093777 A1* | 3/2017 | Neustifter ............... H04L 51/16 |
| 2017/0094023 A1* | 3/2017 | Jack ........................ H04L 51/10 |
| 2017/0357903 A1* | 12/2017 | Pal ........................... G06N 5/04 |
| 2019/0174289 A1* | 6/2019 | Martin ................. H04M 3/5116 |
| 2019/0282155 A1* | 9/2019 | St Amant ............... A61B 5/165 |

* cited by examiner

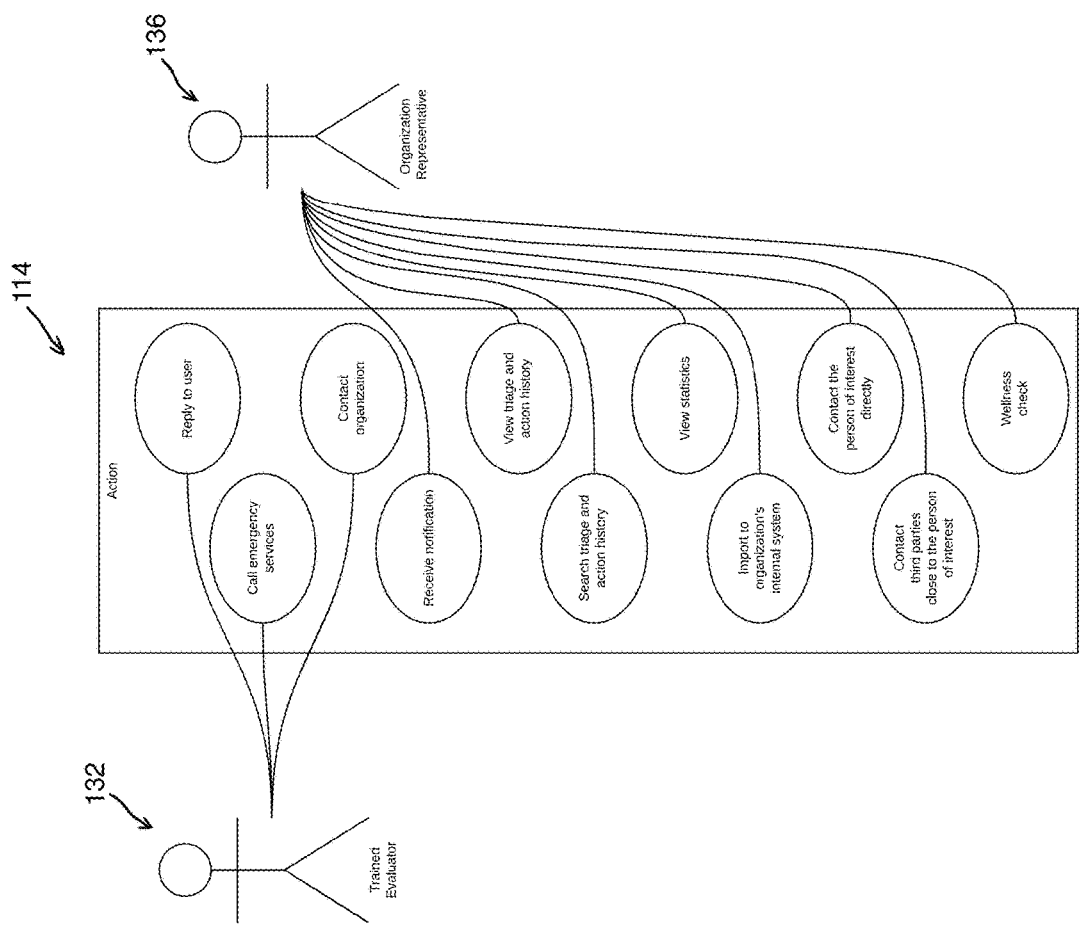

SOCIAL MEDIA MONITORING SYSTEM AND METHOD

PRIORITY

This application claims priority to and the benefit of U.S. Provisional Patent Application No. 62/644,719, filed Mar. 19, 2018, which is incorporated fully herein by reference.

TECHNICAL FIELD

The present invention relates generally to systems, methods, and computer programs for monitoring social media, or other electronic document or data accounts or services, using automated and manual review systems and methods.

BACKGROUND OF THE INVENTION

There are current needs for monitoring users or user messages on various social media platforms—e.g., Twitter®, Facebook®, Instagram®, Reddit®, Snapchat®, WhatsApp®, Google+®, YouTube®, etc. Organizations, such as schools, businesses, government institutions, and the like, may desire to monitor a student athlete's social media activity for rules violations, the general or a target population for threats of violence, students or other citizens for indications of bullying, violations, suicidality, and the like. Current attempts to monitor social media accounts are very limited and can often be cumbersome and ineffective.

Accordingly, there exists a need for new, improved, and more efficient systems and methods to optimize allocation of resources to maximize the recall of relevant social media content in a timely manner.

SUMMARY OF THE INVENTION

Particular embodiments of the system of the present invention are adapted to monitor one or more social media accounts, or other electronically stored information, of one or more users to process and identify important, suspicious, or concerning activity, or even activity determined to be particularly relevant under given circumstances. The system can employ automated filtering methods to select from all social media activity the data that is most likely to be relevant for review. In many cases, search strings and keywords may not achieve sufficient discrimination. Accordingly, it may be desirable to use machine learning methods of the invention to process and learn more sophisticated rules to filter relevant content and information. In some cases, the content of a post may be ambiguous in isolation—e.g., by referencing previous posts. Therefore, it can be desirable to retrieve and use context, such as other posts from the same user or replies from other users, in sophisticated machine learning filters.

The system of the present invention can include a firehose filter, a single post machine learning filter, a contextual machine learning filter, and a target population machine learning filter. The social media post data can be filtered through a firehose content filter, into the single post machine learning filter, into the contextual machine learning filter, and then to the target population machine learning filter. Alternatively, the social media post data is first filtered through a firehose population filter, then into the single post machine learning filter, and then to the contextual machine learning filter.

With various embodiments, the filtered post data (e.g., passed or processed through the plurality of filters) is directed to a triage queue. Alternatively, post data may skip through a plurality of filters through a sampling process. Posts in the triage queue are prioritized, assigned for review, and go through a triage process where reviewers label them. Results from the triage can be stored to a triage database. From there, various actions can take place for storage at an action database. Trained evaluators, supervisors, organization representatives, and like staff or personnel can perform triage tasks and actions based on relevancy and information received through the system from the social media content or author.

The above and other aspects and embodiments of the present invention are described below with reference to the accompanying drawings.

BRIEF DESCRIPTION OF THE DRAWINGS

The accompanying drawings, which are incorporated herein and form part of the specification, illustrate various embodiments of the present disclosure and, together with the description, further explain the principles of the disclosure and to enable a person skilled in the pertinent art to make and use the embodiments disclosed herein. In the drawings, like reference numbers indicate identical or functionally similar elements.

FIG. 14 shows a diagram of actions or responses performed by trained evaluators and/or organization representatives in a system of monitoring social media accounts and posts, in accordance with embodiments of the present invention.

DETAILED DESCRIPTION

Figure 1:
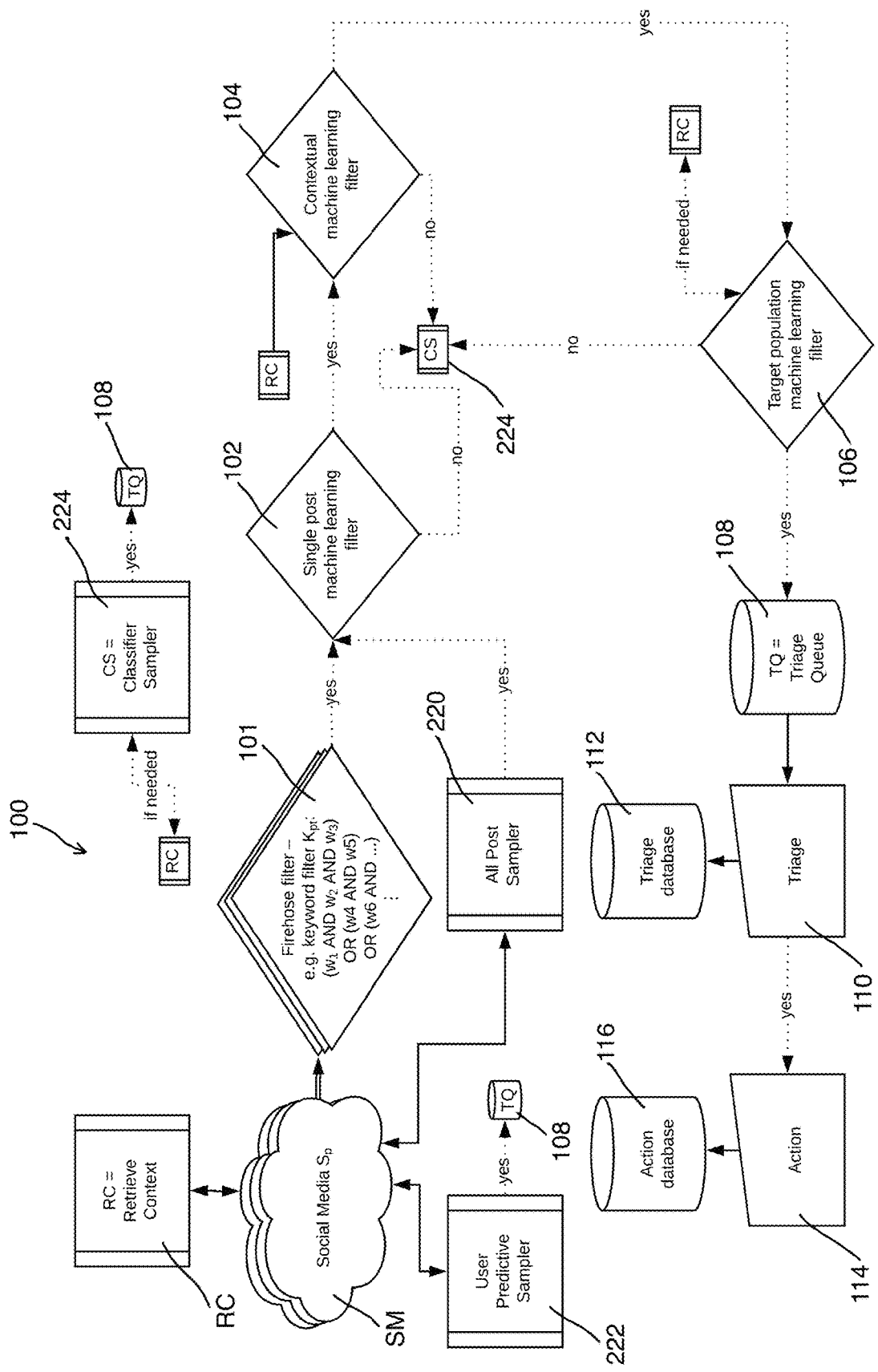
FIGS. 1-2 show exemplary diagrams of systems of monitoring social media accounts and posts, in accordance with embodiments of the present invention.

Referring generally to FIGS. 1-14, exemplary methods, modules, and computer programs, or software application systems 100 are configured to monitor one or more social media accounts, or other electronically stored information (e.g., electronic documents), of one or more users to process and identify important, suspicious, or concerning activity, or even activity determined to be particularly relevant under given circumstances. Exemplary social media accounts or servers can include Twitter®, Facebook®, Instagram®, Reddit®, Snapchat®, WhatsApp®, Google+®, YouTube®, etc.

Organizations and entities may be interested in monitoring social media sites for relevant activity for which certain assertions hold about the content and author of the electronic post. Multiple organizations may be interested in the same type of posts (content) but from different user populations (authors/users). Examples may include schools that wish to be informed of instances of bullying amongst their students; NCAA institutions that wish to monitor their student athletes' social media activity for potential rules violations; public safety organizations that wish to monitor the local or a target population for threats of violence; colleges or other institutions/entities that wish to monitor their student population for indications of suicidality; and the like.

In various cases, such as those identified herein and others, automated methods alone may not be enough to identify relevant data with sufficient discrimination. Accordingly, it may be necessary for a person, or persons, to review the data to determine relevancy and the appropriate response (e.g., via a triage process). However, the number of person-hours that can be allocated to this task is a limited resource and can be a bottleneck in the process. As such, it would not be feasible to have a person review all social media activity for relevancy.

The system 100 of the present invention utilizes automated filtering methods to select, from all social media activity, or other electronically stored information, the data that is most likely to be relevant for triage review. Due to the volume of social media activity, the initial firehose filter that is applied to all activity on the social media service needs to be simple and efficient, such as a keyword filter. In many cases, such as the examples above, simple filters such as search strings and keywords may not achieve sufficient discrimination. There may be many manifestations or expressions of a particular type (e.g., disclosure of suicidal ideation) which are not well separated or understood by keywords alone. Accordingly, it is desirable to use machine learning methods of the present invention to process and learn more sophisticated rules to filter relevant content. In some cases, the content of a post may be ambiguous or appear benign in isolation—e.g., by referencing previous posts. Therefore, the system 100 can retrieve and use context, such as other posts from the same user or replies from other users, and use this information in a sophisticated machine learning filter. The retrieval of contextual information via API calls to the social media service may be a bottleneck and so the machine learning filter that incorporates such contextual information may be preceded by a single post machine learning filter that utilizes only the data in the post object from that received from the firehose filter (possibly with previously stored information).

There may be spikes in social media activity related to current events (e.g., a celebrity suicide; release of a trailer for Suicide Squad movie, etc.) or memes (e.g., Evil Kermit) that produce false positives. It would be undesirable to waste time and resources reviewing many posts about the same trending topic, or to generate a lot of training data that will bias the filters once the spike has passed. Therefore, the system 100 can also include a mechanism, such as an optional clustering module or filter, to cluster non-relevant messages or posts—e.g., that are part of a non-relevant trending or similar types of topics (e.g., Suicide Squad movie trailer) prior to processing the post data through the one or more content filters. The single post filter and the contextual filter are configured to identify and process potentially relevant classes or posts (e.g., suicidal ideation), wherein the clustering module is configured to filter out the large number of non-relevant posts or classes.

The clustering filter can identify messages related to the same current event or meme. This may be done by comparing the string similarity of the candidate post with previous posts that have been marked as false positives to find duplicates or near duplicates. It can also process and check image similarity (e.g., to identify image macros) and similarity of linked websites (e.g., news stories). Keywords, phrases, and hashtags that have experienced a spike in usage and occur in false positive posts can be candidates for cluster markers. Candidate posts may be accepted or rejected by the trained staff during triage review. Cluster markers may be suggested directly by the trained staff as well. Once a message has been matched with a false positive cluster, it may be filtered out. Otherwise, it is passed on or communicated to the next filtering module in the system 100. When activity related to a given cluster fades, that cluster may be eliminated or retired. This clustering module processes and deals with the instability of the negative class. It is expected that the positive class will be relatively stable. There is likely more conceptual drift in the non-relevant items due to trending topics and removing these posts before reaching the relevant content filters creates a more stable distribution. Conceptual drift, or concept drift, is when distribution of data input to a classifier changes over time. For user authored content, the subjects they discuss or the way that they talk about those subjects may change. This can pose a problem for the classifier which was machine trained on a data distribution that differs from the current distribution. It can be expected that some classes might be more stable than others. For instance, suicidal ideation is likely to be relatively stable as compared to the distribution of all other posts (the negative class).

Some relevant posts may be higher priority than others. For example, of posts disclosing suicidal ideation, those expressing intent are higher priority than those that do not. Accordingly, the system 100 can include a prioritization function. Further, users in the target population may not self-identify as such in their profile (e.g., student at University of XYZ) and also cannot be sufficiently discriminated or identified with search strings and keywords. As such, the system 100 can include machine learning to identify users of interest. Embodiments of the present invention can apply such a population filter on all social network users, such that the system 100 uses a network sampling strategy to propose candidate users for review, by a trained evaluator or reviewer at the triage process further detailed herein.

Figure 2:
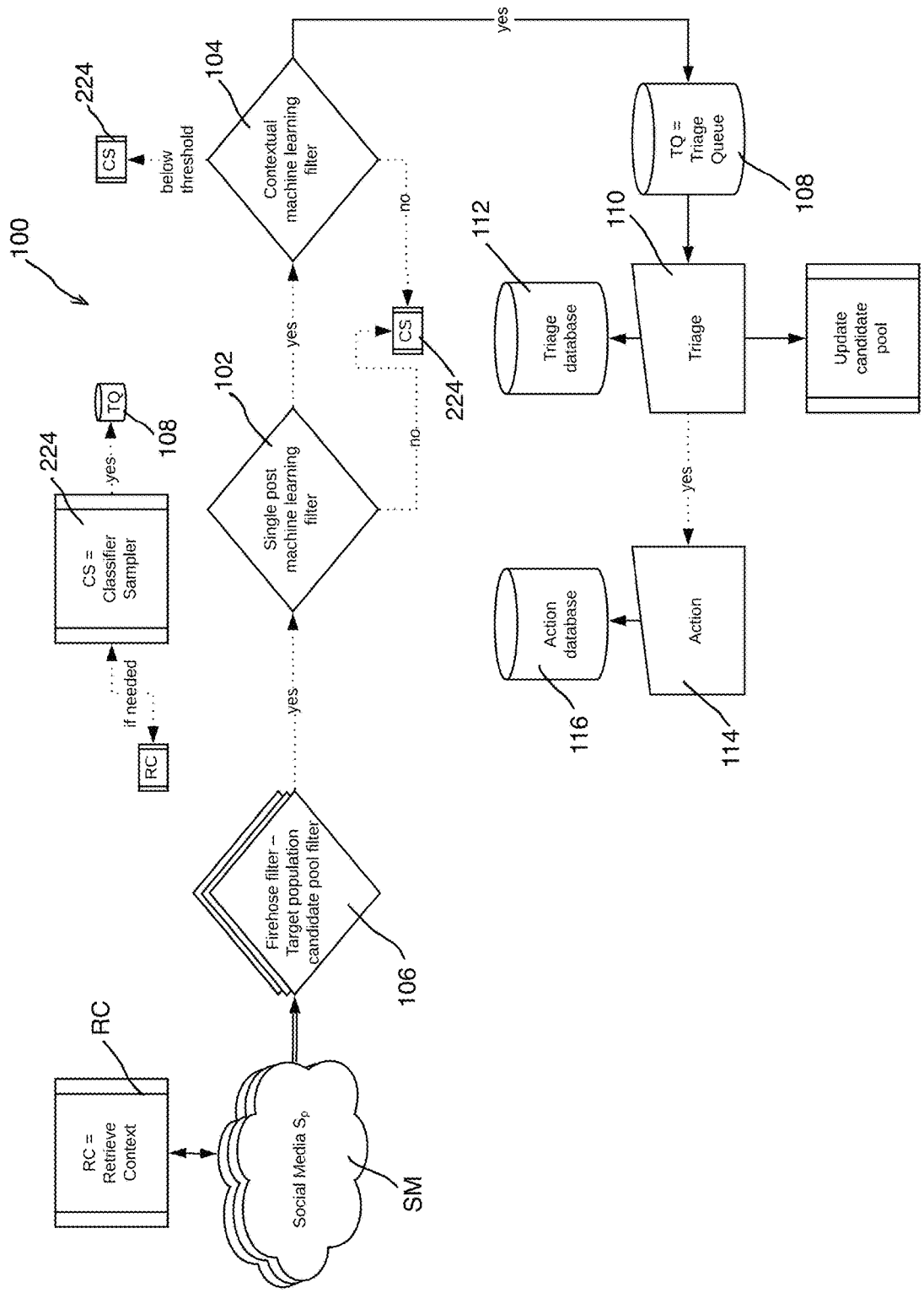

Referring generally to FIGS. 1-2, in accordance with various embodiments, the system 100 can include a firehose filter or module 101, a single post machine learning filter or module 102, a contextual machine learning filter or module 104, and a target population machine learning filter or module 106. These filters/modules 102, 104, 106 include various sub-modules (e.g., feature extractors, classifiers, etc.) as detailed further herein.

FIG. 1 shows social media SM data or posts received into the system 100 for processing, wherein the post data is filtered through a firehose content filter, into the single post machine learning filter 102, into the contextual machine learning filter 104, and then to the target population machine learning filter 106. FIG. 2 shows inputting of the social media SM data first through a firehose population filter 106, into the single post machine learning filter 102, and then the contextual machine learning filter 104 as disclosed further herein.

With various embodiments, the filtered post data (e.g., passed or processed through the plurality of filters) is directed to a triage queue 108. Alternatively, post data may skip through a plurality of filters through a sampling process. Posts in the triage queue are prioritized, assigned for review, then go to a triage process 110 for review by the trained evaluators/reviewers. Results from the triage 110 can be stored to a triage database 112. From there, various actions can take place and stored at an action database 116. Further details of the triage process are provided herein.

While there can be inherent resource limitations in terms of data requests, processing power, storage capacity, and the budget to expend on these various features, the modules or filters of the present invention can be combined in various ways to best utilize the available resources. These methods are described in more detail herein, along with examples of how they may be combined.

The filters only guarantee to pass on items that are above threshold and items may be sampled to skip one or more filters for various reasons. Sampling may be used to test the recall or calibration of a classifier, for active learning, or to measure inter-rater reliability. A sampling scheduler is used to coordinate the samplers. The sampler has a long-term target of what percentage of the labeling efforts should go towards improving the overall system by, for example, calibration or active learning, and adapts to short-term variation in capacity and throughput (e.g., sampling more when there is excess capacity; less or none when labelers are not keeping up and there is a backlog growing in the triage queue, etc.). The probability of sampling may be inversely related to the stable velocity of the below-threshold items (e.g., so the system is not swamped by the class imbalance) and inversely related to the temporal change in the velocity of the above-threshold items (e.g., to take advantage of when there are lulls). These samples can also be used (and oversampled) in machine training to counteract the selection bias from training with items selected to be reviewed by the filter.

Sampled items are scored by the machine classifiers described herein, but may go directly to the triage queue 108 or pass on to the next filter regardless of their score. Items which do not pass a filter may go to the corresponding classifier sampler 224, e.g., CS in the figures. Alternatively, the classifier sampler 224 may be applied before the filter. Classifier samplers 224 may be used for calibration of the machine learning classifier and/or for active learning. Items that are sampled will skip all filters to go directly to the triage queue 108 unless the class imbalance is too great. That is to say, the prevalence of the target items is too low for useful direct random sampling. This would be expected in the case of the firehose filter 101. To deal with this a trade-off may be made to use a biased sample in order to obtain higher prevalence. This may be done by skipping only a single filter and not passing items directly to the triage queue 108, as in the case of the all post sampler 220. An item sampled in this manner might not make it through subsequent filters and is, therefore, not guaranteed to be reviewed, but this method still provides a way to identify false negatives for a given filter, just only the ones that are also true positives for all subsequent filters.

Another way to deal with the problem of the class imbalance at the firehose filter 101 is to implement another way to identify posts that are likely to be relevant not based on the content. The user predictive sampler works by sampling messages from accounts or users that have previously posted a relevant message and are more likely to post such a message again. The system 100 can predict for given users (e.g., from the candidate pool) based on their past posting history, the probability that their next post will be relevant and sampled based on that probability. This gives an upper bound on the recall of the firehose filter 101 and also can identify keyword filter false negatives that can be used to automatically improve that filter. Common terms from keyword filter false negatives identified in this way can be used in a multi-arm bandit to test query expansions. Further details are provided for the sampling methodology with reference to FIG. 11.

Retrieve context RC indicates that more API calls need to be made to the social media account or service SM to gather additional information beyond the data included in the post object retrieved via the keyword filtering (filter 101) or target population filtering (filter 106) described herein. For example, this would be utilized to get the image from media posts, to gather and process previous posts by the same user, to check for replies by other users, etc.

Firehose Filter

The firehose filter 101 can be applied to all posts on a social media site. This can be a keyword or search phrase content filter (e.g., FIG. 1) that is in communication through the API of the social media site itself or a data provider. If the target population is small enough, the firehose filter can be a population filter 106 rather than a content filter (e.g., FIG. 2), keeping only posts authored by users above the threshold in the candidate pool. If the resources are available, the firehose filter 101 can be a fast and efficient classifier that utilizes simple features and a shallow model, such as FastText or other like features and models.

FIGS. 3-11 detail exemplary embodiments of various filtering and sampler functions or modules implemented within the system 100.

Single Post Filter

Figure 3:
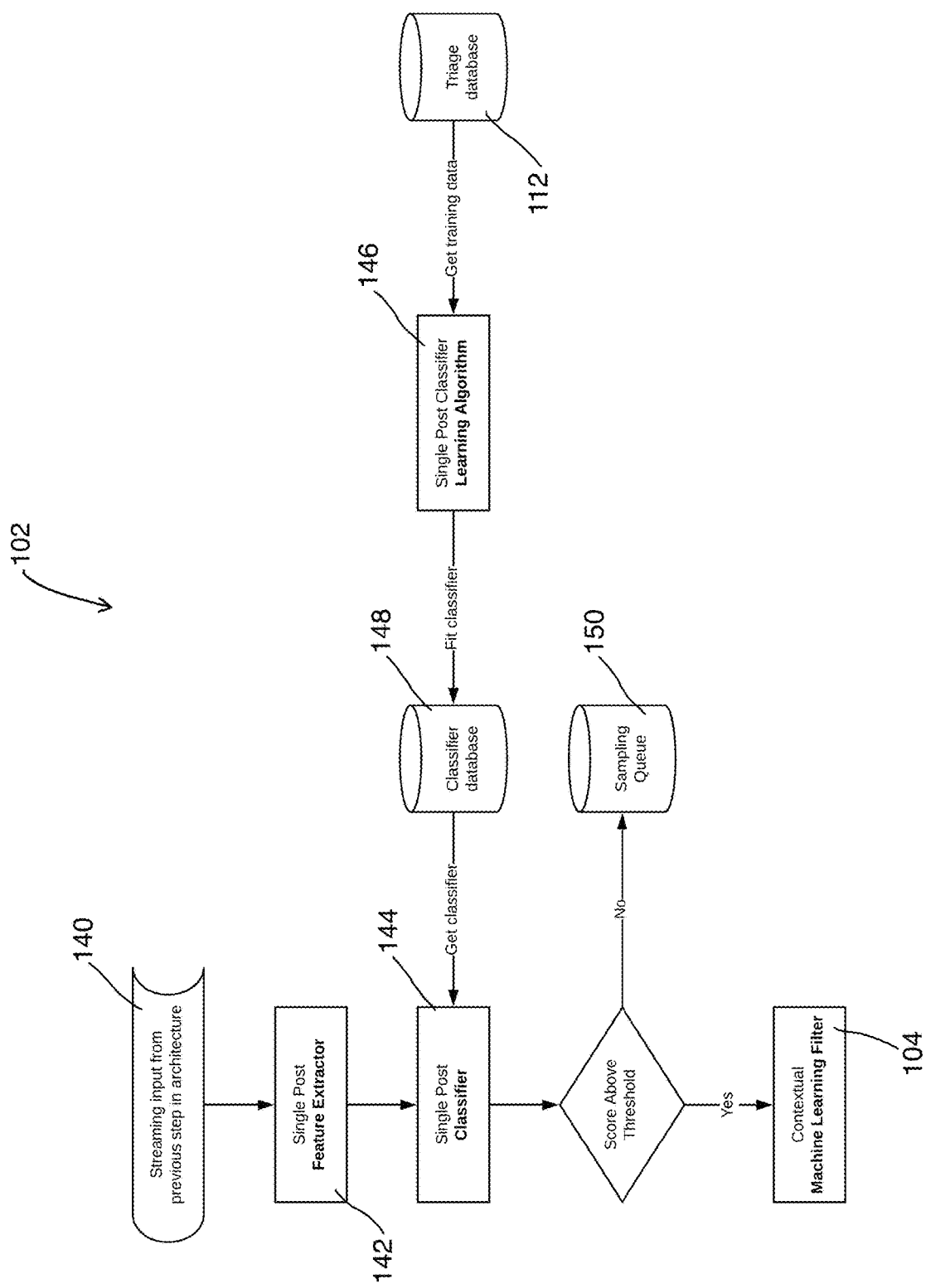
FIG. 3 shows a diagram of a single post filter process in a system of monitoring social media accounts and posts, in accordance with embodiments of the present invention.
Figure 4:
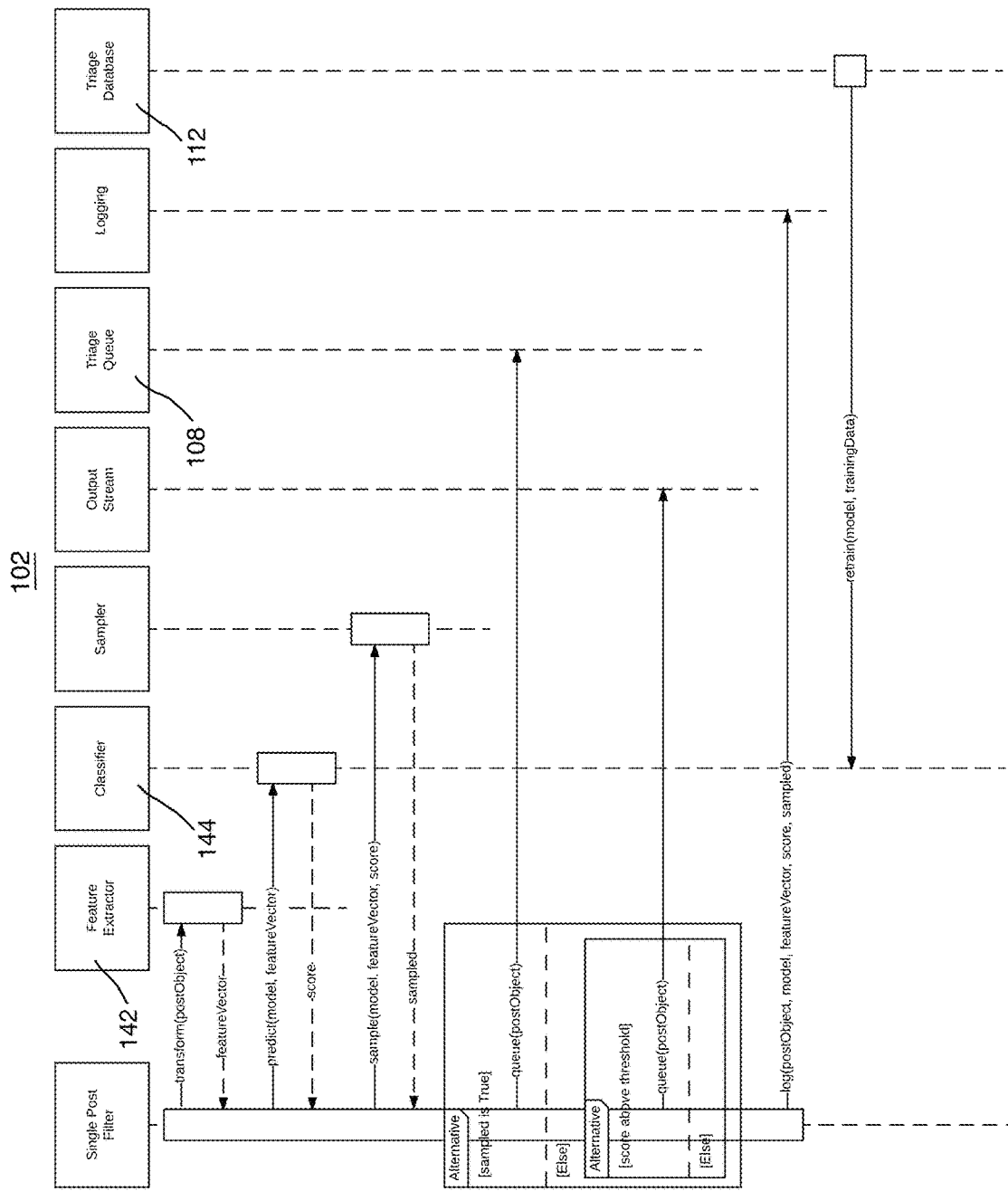
FIG. 4 shows a sequence diagram for a single post filter process in a system of monitoring social media accounts and posts, in accordance with embodiments of the present invention.

As detailed in FIGS. 3-4, the single post filter 102 can process and construct features from any data contained in a single post object. These features are then fed or otherwise communicated to a machine learning classifier. Such data may include the text of the post, the number of times the post has been liked or shared, the time the post was created, amongst a myriad of other data. The classifier processes and assigns a probability to multiple relevant and non-relevant subclasses. If the probability of relevance is above a predetermined threshold, then it is passed on or communicated to the next module, such as the contextual filter 104.

As shown for the exemplary embodiment of FIG. 3, data is inputted into the single post machine learning filter 102 from a previous step in the system 100 architecture. A single post feature extractor is performed at step 142 and feeds into a single post classifier 144. The feature extractor provides a representation of the object for the classifier 144. The classifier 144 scores relevance of the post. Data or information from the triage database 112 is inputted into and processed at a single post classifier learning algorithm 146, and then stored at a classifier database 148. The learning algorithm 146 sets the parameters for the classifier 144. That information data is processed at the classifier 144 to determine if it includes a score above a predetermined threshold. If no, the data is stored in a sampling queue 150. If yes, the data is further fed to the contextual machine learning filter module 104.

The learning algorithm 146 of the single post filter 102 can be executed continuously (e.g., for an online machine learning method), but in many instances or applications it would not be. If it is not an online learning method, then the classifier would be retrained in batch as opposed to being updated for every incoming item. This retraining can occur periodically, such as once a day, once a week, etc.

Contextual Filter

Figure 5:
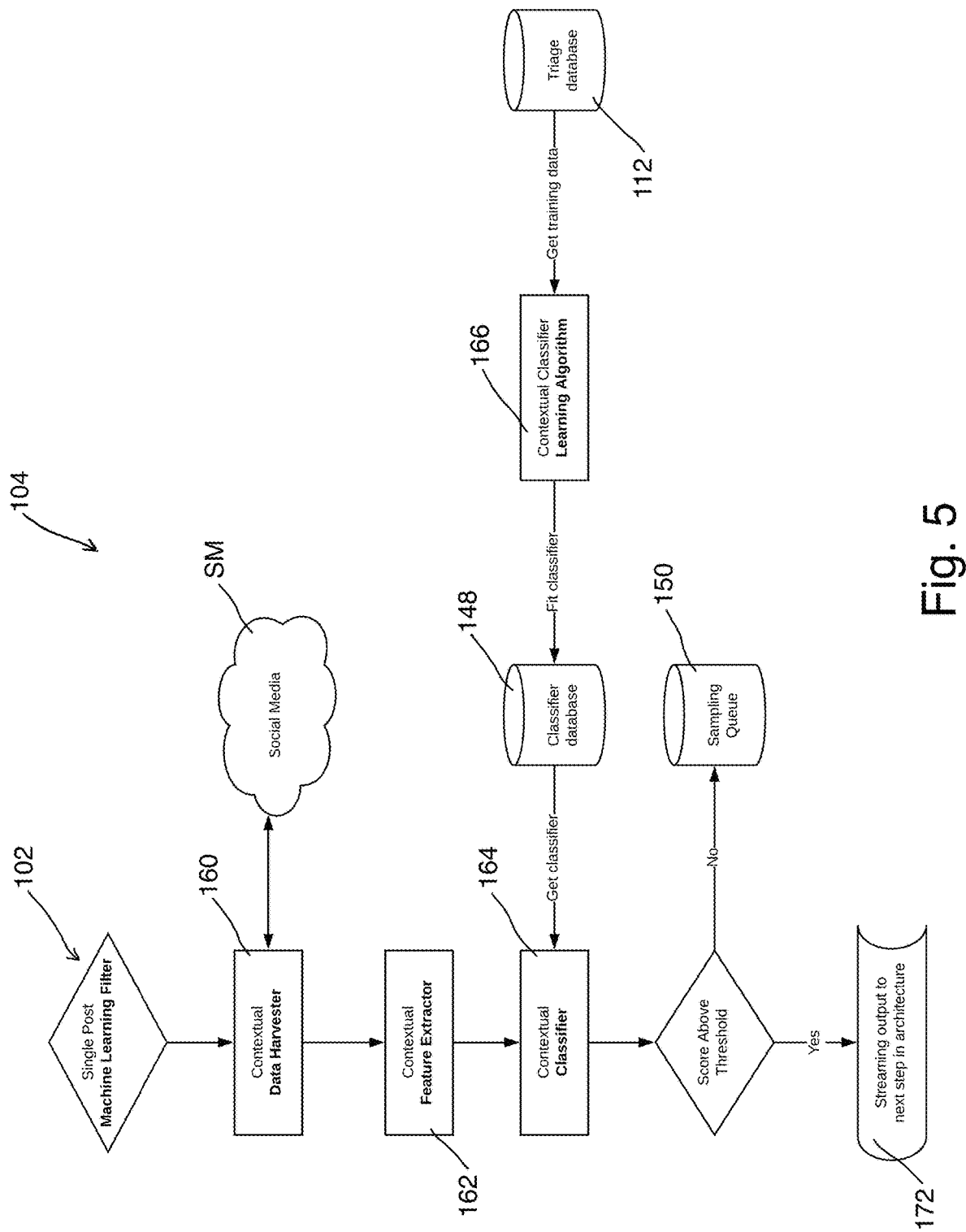
FIG. 5 shows a diagram of a contextual filter process in a system of monitoring social media accounts and posts, in accordance with embodiments of the present invention.
Figure 6:
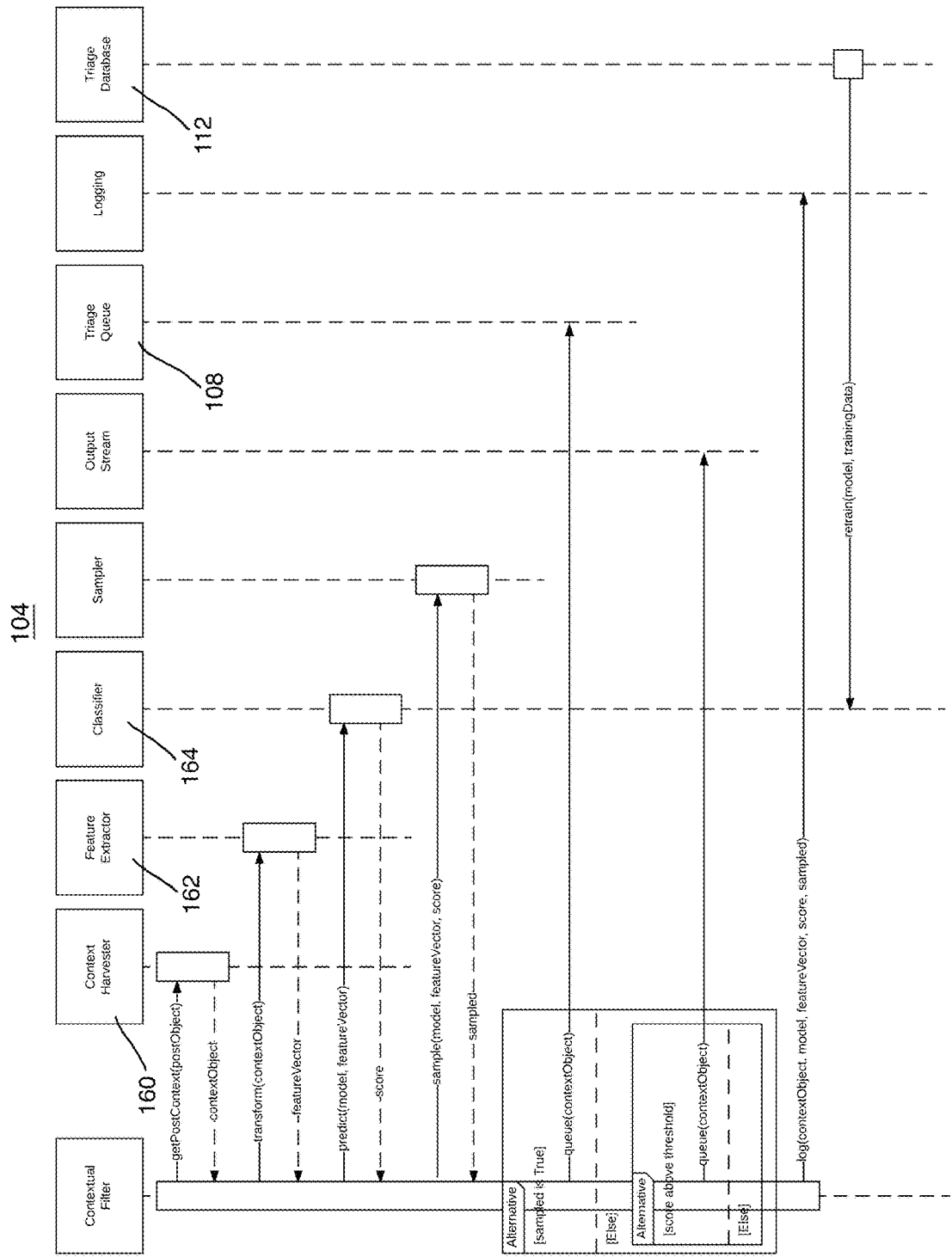
FIG. 6 shows a sequence diagram for a contextual filter process in a system of monitoring social media accounts, in accordance with embodiments of the present invention.

The contextual machine learning filter 104, as depicted in FIGS. 5-6, is adapted to gather and process additional data beyond the single post filter 102 to augment the classification decision. Such data may include previous and subsequent posts by the same user, threads that the user participated in by replying and/or being replied to, the content of web pages that are linked in a post, amongst other information—e.g., information or objects beyond the actual text of the post. Features are constructed from this data and then fed or communicated to machine learning classifiers. Classifiers may be used to identify and categorize relevant contextual evidence (e.g., posts revealing risk factors). The overall classifier may assign a probability to multiple relevant and non-relevant subclasses. If the probability of relevance is above a predetermined threshold, then the item is passed on or communicated to the next module.

For example, as shown in FIG. 5, data can be inputted into the contextual machine learning filter 104 from the single post learning filter 102. A contextual data harvester 160 is executed and is in communications with the social media SM account or service. From there, the harvested data is inputted into a contextual feature extractor 162 for processing, which in turn inputs data to the contextual classifier 164. The feature extractor 162 provides a representation of the object for the classifier 164. The classifier 164 scores relevance of the data. Data from the triage database 112 is inputted into and processed at a contextual classifier learning algorithm 166, stored at a classifier database 148, and then fed to the contextual classifier 164. If the probability of relevance is above a predetermined threshold, then the item is passed on or communicated to the next module or step in the system 100 architecture. If not, the subject data is stored in the sampling queue 150.

The learning algorithm 166 of the contextual filter 104 sets the parameters for the classifier 164. The algorithm 166 can be executed continuously (e.g., for an online machine learning method), but in many instances or applications it would not be. If it is not an online learning method, then the classifier 164 would be retrained in batch from the algorithm 166, as opposed to being updated for every incoming item. This retraining can occur periodically, such as once a day, once a week, etc.

Population Filter

Referring generally to FIGS. 7-10, the population filter 106 stores and maintains a set of users that have been assigned a machine classified and/or human annotated probability of being in the target population. This set of users is referred to as the candidate pool. The population machine classifier is a relational (or collective) classifier that takes into account the social connectivity of the candidate pool when determining the predicted probabilities, and also uses the post history of the users. Additional classifiers may be used to identify relevant evidence from a user's profile and activity (e.g., bio says user is professor, not a student; post about going to a study session or living in a dorm, etc.). This may include evidence of entrance to the population (e.g., post about orientation) or exit (e.g., post about dropout or graduation). If the probability of the user being in the target population is above a predetermined threshold, then the item is passed on or communicated to the next module.

Resource constraints prevent putting the entire social network in the candidate pool because the system 100 cannot obtain or process the entire social graph and all users' post history. Instead, the system 100 processes and grows the candidate pool over time. The pool may be seeded by keyword searches (e.g., UofXYZ Class of 20XX) or from followers of organization specific accounts (e.g., @UofXYZ). A classifier program is machine trained to snowball sample from the current candidate pool by predicting which users one hop away are most likely to be in the target population. Classifiers may also be machine trained to continue expansion by keyword search.

Given that the contextual classifier already collects social media post history, the system 100 software can train a non-relational (or non-collective) population classifier to identify users who may be likely to be in the target population based on post history and profile info, but either are not connected to any of the users in the candidate pool or the connectivity results in a low score by the snowball classifier.

The population filter 106 can be optional with embodiments of the system 100, such as when it is unnecessary if the target population is "all users" or is achievable by a content filter, e.g., English speaking users, English language content, etc.). In the embodiment where content filtering occurs before the population filter 106, a non-relational user filter is also optional. Without it, users not in the candidate pool are all filtered out.

Figure 7:
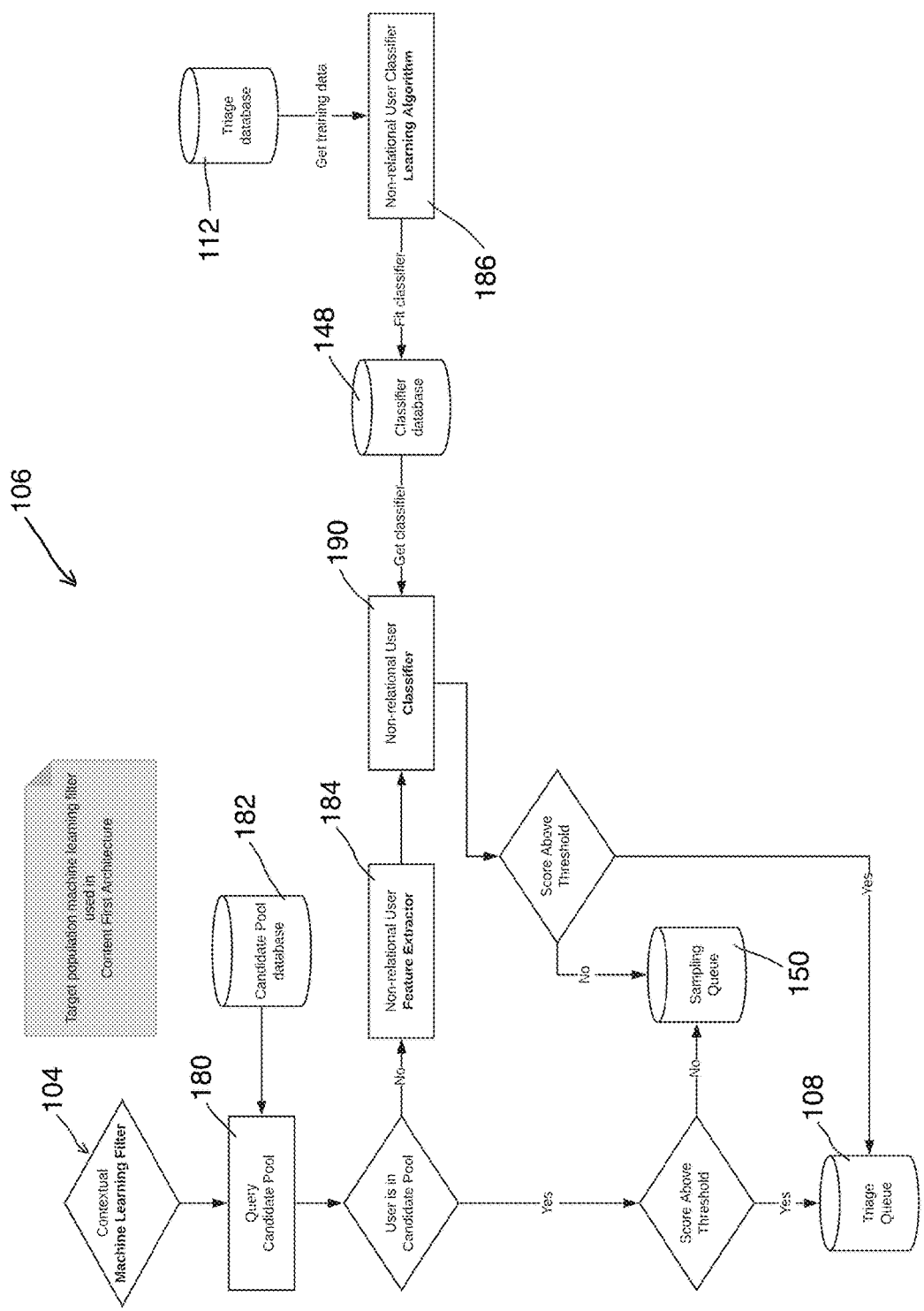
FIG. 7 shows a diagram of a target population filter process in a system of monitoring social media accounts and posts using a content first architecture, in accordance with embodiments of the present invention.

FIG. 7 demonstrates operation of the target population machine learning filter 106 under a system 100 architecture where content processing and filtering precedes the population filter 106 (e.g., FIG. 1). First, data is inputted into the target population machine learning filter 106 from the contextual machine learning filter 104. Next, the candidate pool database 182 is queried at step 180. That data is processed to determine if a particular user is in the candidate pool. If not, a non-relational (or non-collective) user feature extractor 184 can be executed, which takes the data about the user and transforms it to create a representation of the data to use as input to the non-relational (or non-collective) user classifier 190. Examples of data about the user can include information from their profile, such as time zone, header photo, and bio; information from posts they have authored; relational information such as links or interactions with other users; etc. The non-relational classifier 190 can use such relational data as input. The non-relational classifier 190 here is a classifier that does not implement collective classification. In addition, data from the triage database 112 is inputted, along with feature representations of training data, into and processed at a non-relational user classifier learning algorithm 186 to produce a trained model, the trained model is stored at a classifier database 148, and then used as the non-relational user classifier 190.

The non-relational user classifier learning algorithm 186 takes the labels from the triage database 112 and the feature representations of labeled data and, in the case of semi-supervised learning methods, unlabeled data to produce learned models which will then be used to classify unlabeled data (a process that can also be employed with the single post and contextual classifiers described herein). It is possible to use as the "non-relational classifier" the model from the relational classifier learned on users in the candidate pool and apply it to users not in the candidate pool, but without updating the collective classification. However, it can be optimal in various embodiments to employ a separate classifier to be used for users not in the candidate pool as it can rely on a reduced feature set that requires fewer resources, e.g., API requests in particular. Users not in the candidate pool that end up being labeled, whether by being fed to the triage queue by passing through the filters or by being sampled, are immediately added to the candidate pool.

Referring back to the step of identifying if the user is in the candidate pool, if the user is in the candidate pool, a determination is made as to whether a resulting score is above the predetermined threshold. If no, the data is stored in the sampling queue 150. If the score is above the threshold, the data is stored in the triage queue 108. Again, the non-relational classifier 190 identifies users who may be likely to be in the target population based on post history and profile info, but either are not connected to any of the users in the candidate pool or the connectivity results in a low score by the snowball classifier. The predetermined threshold can vary dynamically based on present conditions, such as triage backlog and other considerations.

Figure 8:
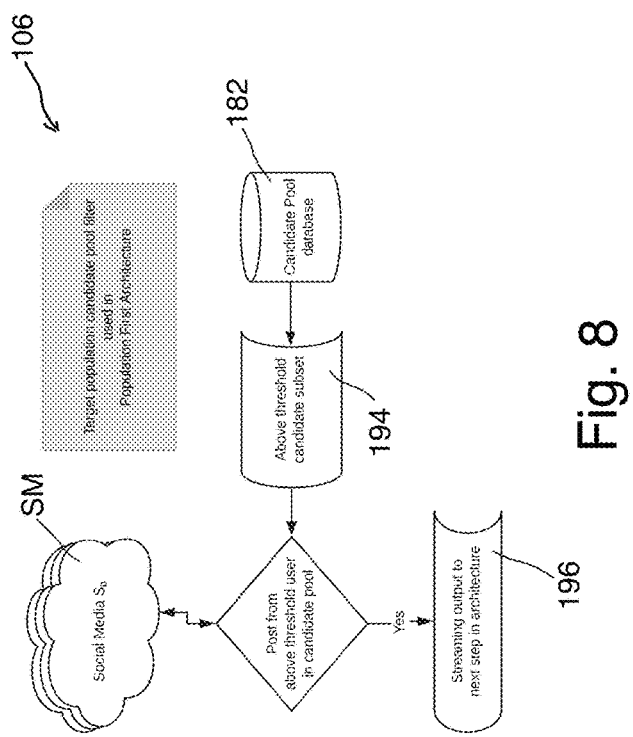
FIG. 8 shows a diagram of a target population filter process in a system of monitoring social media accounts and posts using a population first architecture, in accordance with embodiments of the present invention.

FIG. 8 demonstrates operation of the target population machine learning filter 106 under a system 100 architecture where the population filter 106 occurs prior to content processing (e.g., FIG. 2). Social media SM post data is received and processed, and a determination is made as to whether the post is from an above-threshold user in the candidate pool. The candidate pool database 182 is processed to deliver an above-threshold candidate subset to facilitate this determination at step 194. If the post is from an above-threshold user in the pool, output is streamed at step 196 to the next process in the system 100 architecture.

Figure 9:
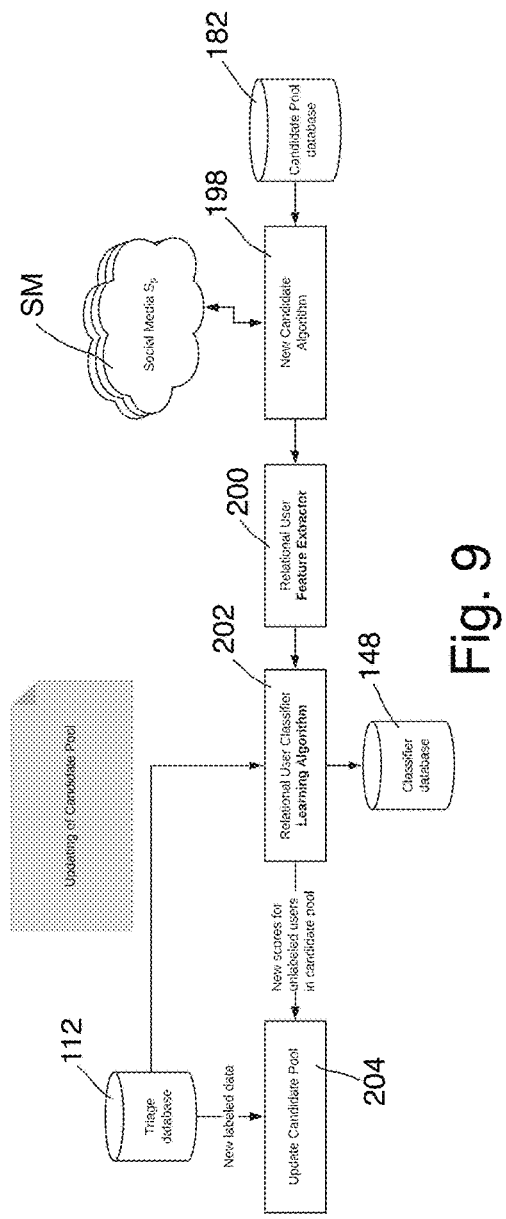
FIG. 9 shows a diagram of candidate pool updating in a system of monitoring social media accounts and posts, in accordance with embodiments of the present invention.
Figure 10:
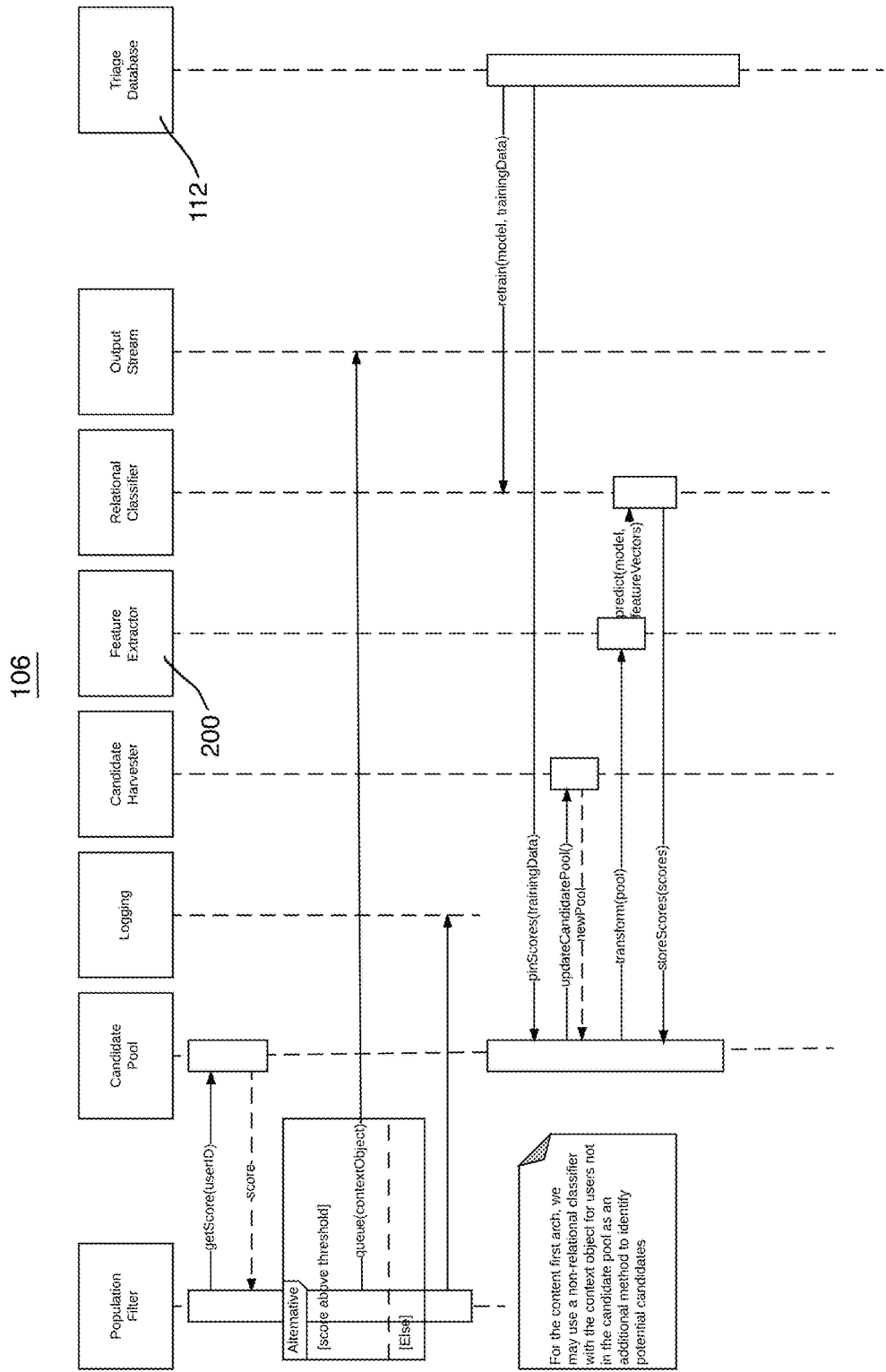
FIG. 10 shows a sequence diagram for a population filter process used in a system of monitoring social media accounts and posts, in accordance with embodiments of the present invention.

FIG. 9 shows the process for updating the candidate pool, in accordance with embodiments of the present invention. In one processing segment, the social media SM data and data from the candidate pool database 182 are fed to and processed at a new candidate algorithm 198, and then through a relational user feature extractor 200 to a relational (or collective) user classifier learning algorithm 202. The relational user feature extractor 200 takes the data about the user and transforms it to create a representation of the data to use as input to the relational user classifier. The relational user classifier learning algorithm 202 takes the labels from the triage database 112 and the feature representations of labeled and unlabeled data to produce learned models which may then be used to classify unlabeled data (a process that can also be employed with the single post and contextual classifiers described herein).

The relational user classifier learning algorithm 202 can use collective classification to jointly classify all users in the candidate pool. In another processing segment, data from the triage database 112 is also inputted to the relational user classifier learning algorithm 202 such that new scores for unlabeled users are processed to update the candidate pool 204. The output from the relational user classifier learning algorithm 202 is also stored in the classifier database 148. Collective classification may be done with new labels before running the new candidate algorithm and then again after adding users to the candidate pool. The new candidate algorithm 198 examines the data on the users currently in the candidate pool and selects new users to add to the candidate pool.

For example, a user that has been labeled as being in the target population or has a high predicted probability of population membership may be used to snowball sample. Namely, the users that they are linked to may be added to the candidate pool. User links might be determined via relations and interactions such as a following, friendship, mentions, and replies. Alternatively, some users may not be in the target population themselves but may be identified to be highly connected to users who are, and these too can be used for snowball sampling. For example, a school's social media account is not a student but it is linked to students. New candidates could be identified by means other than snowball sampling such as by searching profile information or posts for indicators of membership in the target population or by checking group and list memberships.

Sampling Processes

Figure 11:
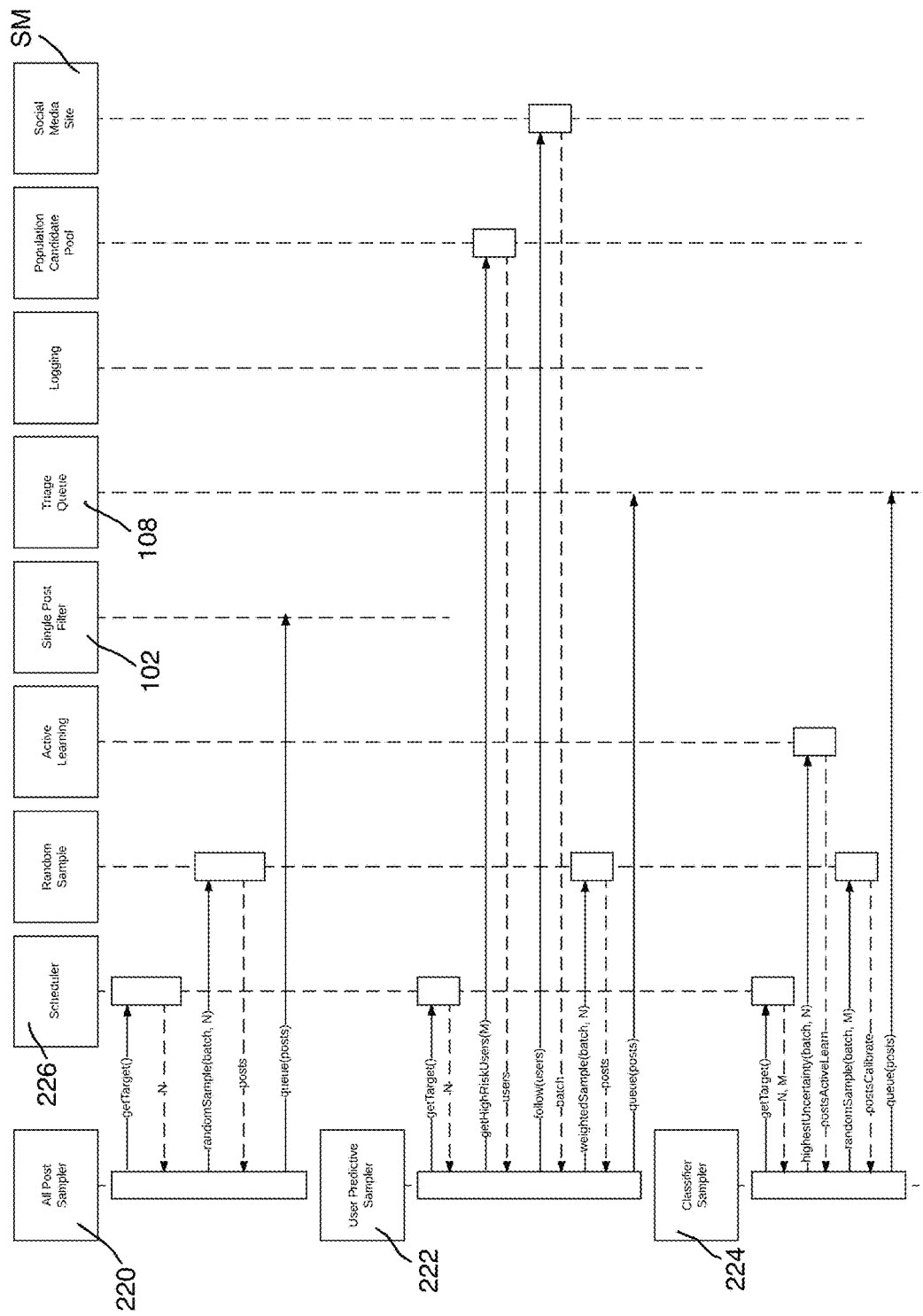
FIG. 11 shows sequence diagrams depicting sampling processes for a system of monitoring social media accounts and posts, in accordance with embodiments of the present invention.

FIG. 11 contains sequence diagrams depicting sampling processes for the system 100. In certain embodiments, the samplers can include an all post sampler 220, a user predictive sampler 222, and classifier samplers 224. These samplers interact with a scheduler 226 to determine the target rate of posts to sample. The scheduler 226 can process and take into account the state of the triage queue 108 and labeling throughput, sampling more when there is excess capacity. The scheduler 226 can also prioritize sampling for calibration of the various system 100 filters that are more susceptible to calibration problems, for example due to concept drift (as defined herein). The scheduler 226 can balance needs for calibration, active learning, and reliability measurement. For calibration of the firehose filter 101, there are two approaches to deal with the fact that prevalence of relevant items may be too low to usefully sample directly from the firehose filter 101 to the triage queue 108.

While the all post sampler 220 does sample directly from the firehose filter 101, the sampled items do not go directly to the triage queue 108. Sampled posts are instead added to the pipeline and may be filtered out without review. The user predictive sampler 222 does not sample from the firehose filter 101, but sampled items are fed directly to the triage queue 108. The user predictive sampler 222 takes posts from users who have posted relevant items in the past and are likely to post more relevant posts in the future. When updating the candidate pool, users may be rated for their likelihood to make new relevant posts and the highly rated users' posts may be collected for weighted sampling according to this likelihood. Alternatively, a triage reviewer 132 may be assigned to triage an entire segment of a user's timeline. Rather than labeling a single post by reviewing it and a small number of surrounding posts for context, the reviewer 132 would instead view a much longer timeline of a user's posts and identify all relevant items.

The classifier sampler 224 can be used for calibration or active learning of a classifier. For calibration of the content and user classifiers, the sampler can use random sampling with all posts in the sampling queue of a given classifier, over a given time period, having equal likelihood of being sampled. For active learning, the sampler will sample the posts for which the classifier was most uncertain. A reliability sampler can also be employed to sample items that have already been labeled at least once in order to measure rater or reviewer reliability. This can be used to identify unreliable raters (possibly for retraining) and to help understand which items raters disagree about and why they disagree.

Triage Process

Figure 12:
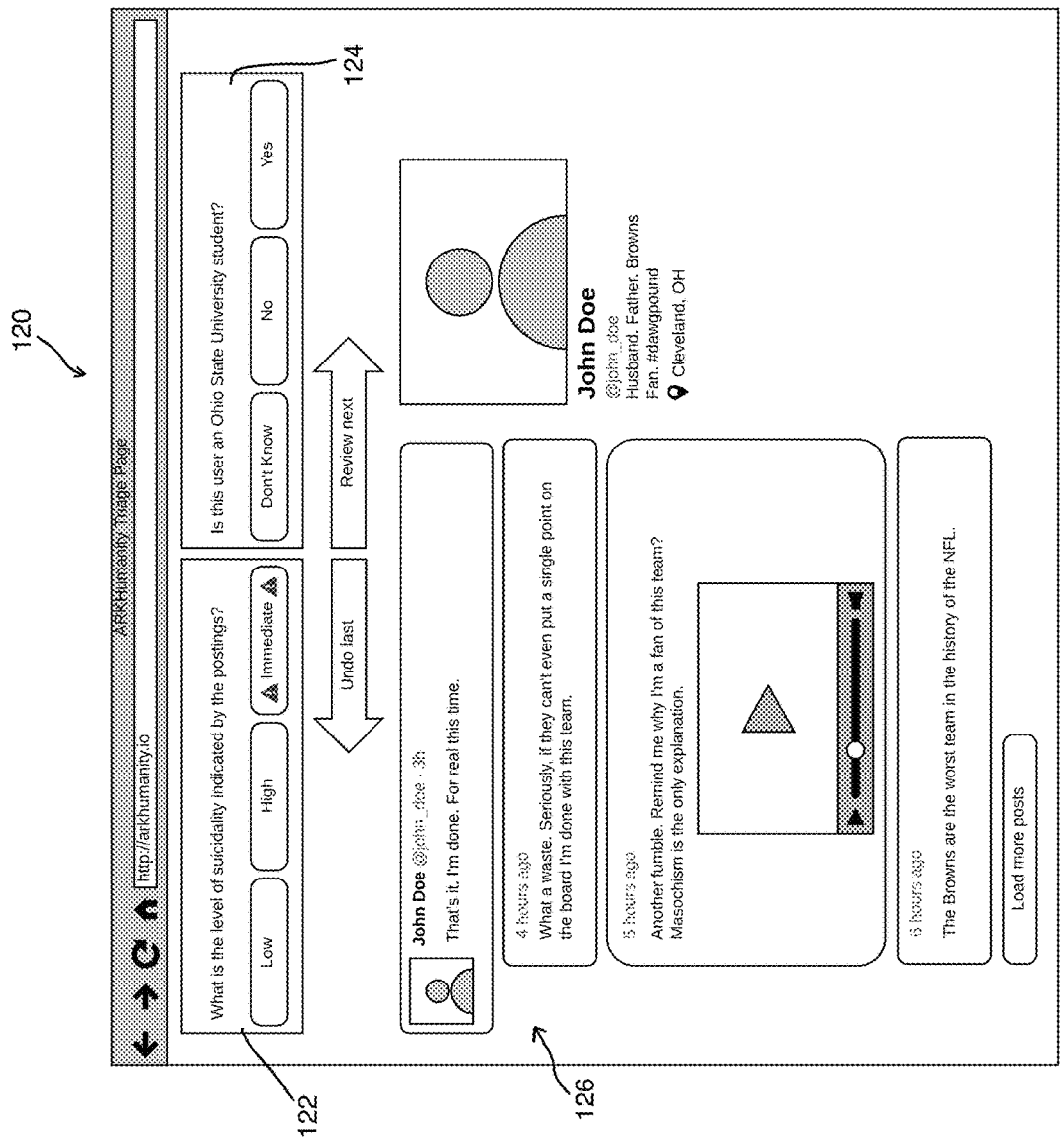
FIG. 12 shows a triage user interface for a system of monitoring social media accounts and posts, in accordance with embodiments of the present invention.
Figure 13:
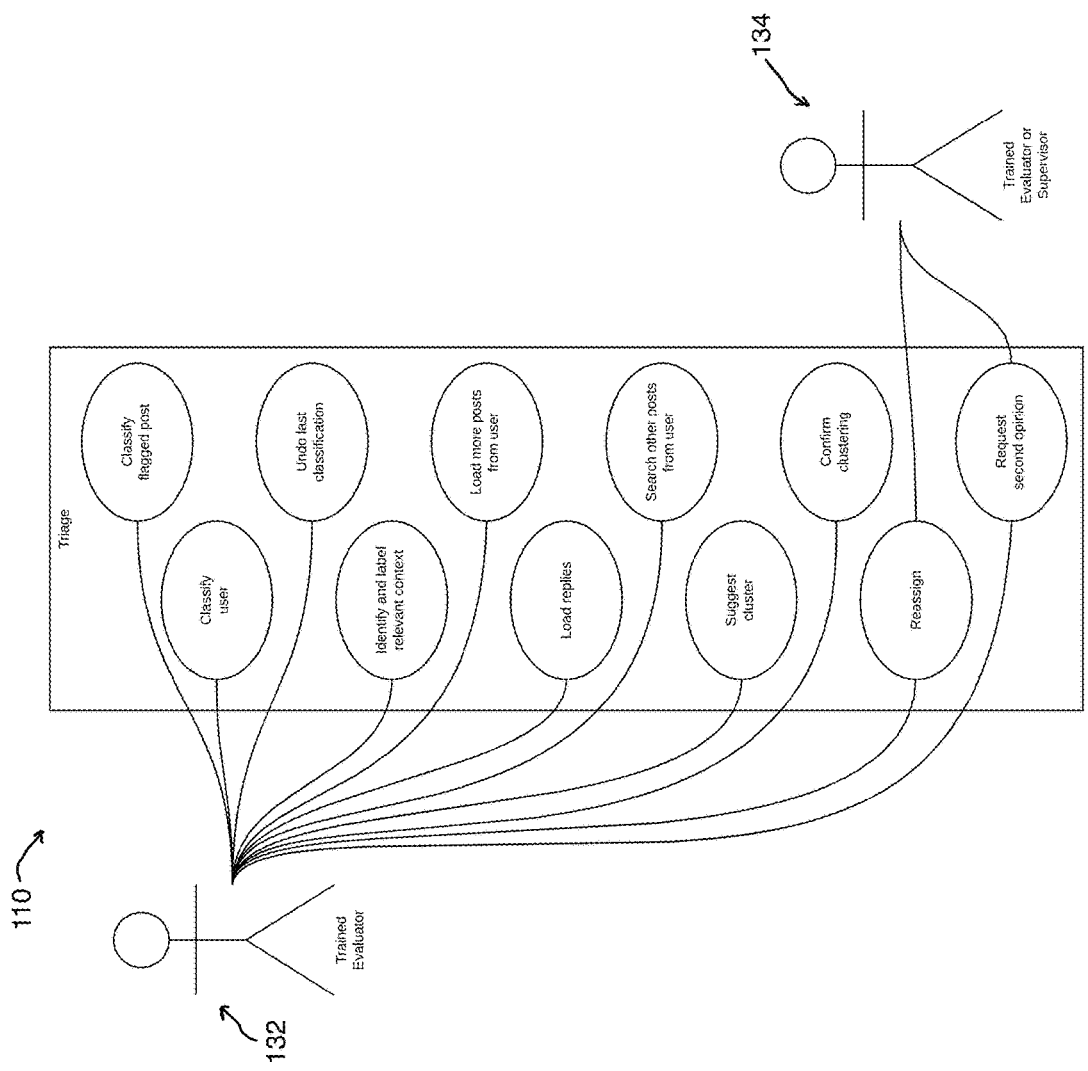
FIG. 13 shows a diagram of a triage tasks performed by trained evaluators and/or supervisors in a system of monitoring social media accounts and posts, in accordance with embodiments of the present invention.

Exemplary triage and action options or methods are detailed further with reference to FIGS. 12-14. Given that multiple organizations may share an interest in identifying posts of a particular type, such organizations may share the usage of content filters and benefit from more training data. To increase reliability, it may be desirable to use trained personnel/staff to review (or, triage) social media SM data using standardized definitions. For example, when reviewing post for indications of suicide risk, the level of risk might be coded as None, Low, Moderate, High, and Immediate, with detailed instructions defining what qualifies for each category. This benefits the organizations by relieving them of the need to review false positives. The trained staff may also annotate contextual evidence, whether supporting (e.g., risk factors) or opposing (e.g., indications of sarcastic or flippant language). Furthermore, the organizations may desire the use of trained staff to take immediate action in cases of urgent need, particularly during off hours. If the machine classifier has a sufficiently high level of confidence that the flagged post is relevant but not urgent, it may skip review by the trained staff.

Representatives of the monitoring organizations can login to the system 100 to view what posts were flagged and any annotations that were made, as well as related statistics. They can take action in response to the flagged posts and record the results.

Items that either passed above the threshold of each filter in the configured setup, or were sampled, are placed into the triage queue 108 for review. The order in which they are retrieved is determined by a prioritization function. If urgency is annotated during review, then the prioritization function can be a machine classifier trained on that label. Otherwise, it may be calculated from a combination of values assigned to the subclasses, weighted based on the predicted subclass probability. The prioritization function may also take into account how recent the post is. Items may be automatically removed from the triage queue 108 if they are deemed to be no longer relevant, e.g., for going too long without review.

A triage user interface 120 is presented on a client device or system that connects to and communicates with the triage queue 108 to retrieve items by priority, as shown in FIG. 12. The interface 120 can be used to review the relevancy of the content and author. With such embodiments, a plurality of reviewer input regions 122, 124 are displayed to receive evaluation information from the reviewer (e.g., level of suicidality, user location, user affiliation, etc.). The user's posting history, personal information, bio, and the like can be displayed in a user details region 126.

The reviewer 132 can undo submitted labels. The reviewer 132 can select amongst subclasses or codes defined in the configuration of the content type. These can be mutually exclusive, or not, and can be annotated with confidence, or not.

The flagged post and several previous and subsequent posts are displayed for review in region 126. The reviewer can load more posts if desired. The reviewer can also search previous posts.

As demonstrated in FIG. 13, the reviewer 132 can perform triage tasks 110. For instance, the reviewer 132 can annotate posts or user info as pertinent and code them according to a supporting evidence schema that was configured for the content type (e.g., risk factors) or target population (e.g., matriculation date). The reviewer 132 can search other posts from the user, suggest a keyword or search phrase to define a cluster of false positives, etc. When a reviewer 132 marks or flags an item as a false positive, if there are similar items in the queue, a potential cluster can be processed and displayed to the reviewer 132 to be accepted or rejected by the reviewer. If the item is determined to be urgent, then the reviewer 132 may take direct action or pass to another on-duty staff member 134 (e.g., trained evaluator or supervisor).

As shown in FIG. 14, possible actions or responses 114 may include replies to the flagged post, direct messages to the flagged user, calls to close friends or family, calls to emergency services, contacting the person of interest directly, contacting third parties close to the person of interest, viewing statistics, performing or initiating a wellness check, and the like.

A default system 100 login interface for the organization representatives 136 is the record of the reviews completed by the trained staff 132, set to display items labeled above that representative's configured thresholds. The interface can also allow the representatives 136 to change the display thresholds and to search the reviews. The representatives 136 can click through or otherwise select a flagged item to view any annotations from the reviewer 132, and to view context, with an option to add the representatives 136 own annotations.

The representatives 136 can export the data, or email or electronically communicate it to, a colleague or entity. The representatives 136 can take actions, such as initiating a wellness check, calling the flagged user or contacting a close friend, family member, or advisor, etc.

If the representative 136 has or gains knowledge that leads to a different categorization of the content type or population membership, then the representative 136 can override the staff reviewer's 132 labels. The system 100 can include an overview interface for each organization to view aggregate statistics.

The representatives 136 can subscribe or unsubscribe to content types. They can set notification preferences to receive text messages, emails, or other electronic communications based on a set criteria. The system 100 can provide administrators with access to an interface to monitor pipeline status and add or modify content type and target population configurations. The classifiers can be retrained periodically and asynchronously.

While the present invention has been primarily explained in terms of its integration or use with social media accounts, this is not meant to be limiting. The software and methods disclosed herein can also be employed with other user or communication services or accounts, including those having electronically stored information such that the system 100 and classifying, filtering, and other disclosed methods of the present invention can be implemented or employed—e.g., with document review systems having authors, users, and the like. For example, for a document review system centering around e-discovery or like methods, the system 100 filters can be employed to receive and process all emails or other electronic documents/data from an author in a given time period to put a given document in context. The contextual data harvester and classifiers of the system 100 can provide a resource intensive second filter that gathers and processes more document data or information.

Various devices or computing systems can be included and adapted to process and carry out the aspects, computations, and algorithmic processing of the system 100 of the present invention. Computing systems and devices of the present invention may include a processor, which may include one or more microprocessors and/or one or more circuits, such as an application specific integrated circuit (ASIC), field-programmable gate arrays (FPGAs), etc. Further, the devices can include a network interface. The network interface is configured to enable communication with the network, other devices and systems, and servers, using a wired and/or wireless connection.

The devices or computing systems may include memory, such as non-transitive memory, which may include one or more non-volatile storage devices and/or one or more volatile storage devices (e.g., random access memory (RAM)). In instances where the devices include a microprocessor, computer readable program code may be stored in a computer readable medium or memory, such as, but not limited to storage media (e.g., a hard disk or solid-state drive), optical media, memory devices (e.g., random access memory, flash memory), etc. The computer program or software code can be stored on a tangible, or non-transitive, machine-readable medium or memory. In some embodiments, computer readable program code is configured such that when executed by a processor, the code causes the device to perform the steps described above and herein. In other embodiments, the device is configured to perform steps described herein without the need for code.

It will be recognized by one skilled in the art that these operations, algorithms, logic, method steps, routines, sub-routines, and modules may be implemented in software, in firmware, in special purpose digital logic, and any combination thereof without deviating from the spirit and scope of the present invention as recited within the claims attached hereto.

The computing devices may include an input device. The input device is configured to receive an input from either a user or a hardware or software component—as disclosed herein in connection with the various user interface or data inputs. Examples of an input device include a keyboard, mouse, microphone, touch screen and software enabling interaction with a touch screen, etc. The devices can also include an output device. Examples of output devices include monitors, televisions, mobile device screens, tablet screens, speakers, remote screens, etc. The output device can be configured to display images, media files, text, or video, or play audio to a user through speaker output.

Server processing systems, for use or connected with the system 100 of the present invention, can include one or more microprocessors, and/or one or more circuits, such as an application specific integrated circuit (ASIC), field-programmable gate arrays (FPGAs), etc. A network interface can be configured to enable communication with the network, using a wired and/or wireless connection, including communication with devices or computing devices disclosed herein. Memory can include one or more non-volatile storage devices and/or one or more volatile storage devices (e.g., random access memory (RAM)). In instances where the server system includes a microprocessor, computer readable program code may be stored in a computer readable medium, such as, but not limited to storage media (e.g., a hard disk or solid-state drive), optical media, memory devices, etc.

The present invention can be embodied as software code residing on a user's computing device (e.g., desktop, tablet, mobile, and the like) and/or on one or more servers. The various data of the present invention can be included on and transferred to and from a storage area network (SAN), a data cloud, or any computing device for storing the file or files being uploaded, downloaded, or processed.

Aspects of the software code of the invention can take the form of a plugin or app, and can interface with various protocols or software using APIs (e.g., social media platforms) or other means of interacting with computing software and systems.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

While the methods, steps, and processing described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of 35 U.S.C. § 112(f) are not to be invoked unless the specific terms "means for" or "step for" are recited in a claim.

What is claimed is:

1. A computer software system of social media account monitoring, comprising:
    a processor and a memory operatively coupled with the processor, such that the processor is configured to execute program code to implement a plurality of filters, the program code comprising:
    a sampling scheduler configured to prioritize sampling based on capacity for processing posts, wherein the sampling scheduler directs post data to input at least a plurality of the plurality of filters, including processed post data from a previous filter, with the sampling scheduler configured to selectively provide instructions to skip one or more of the plurality of filters based on target rates of posts to sample,
    wherein the plurality of filters include:
        one or more firehose filters configured to perform a content search of all social media posts from one or more sources to determine a firehose post data output, including social media post data, to send to the sampling scheduler;
        a single post filter configured to read post data from a single post input to process one or more features from a single social media post object to determine relevant social media posts to include in a single post data output to send to the sampling scheduler;
        a contextual filter configured to read post data from a contextual input to gather and process additional data beyond data processed by the single post filter to augment classification and to include in a contextual post data output to send to the sampling scheduler; and
        a target population filter configured to read post data from a population input to determine if one or more users are to be identified for a target social media user population such that one or more identified users with one or more probability scores are stored in a target candidate pool with other identified users to identify user relevance for additional monitoring or review.

2. The system of claim 1, wherein the target population filter is executed prior to execution of the single post filter.

3. The system of claim 1, wherein the target population filter is executed after the execution of the contextual filter.

4. The system of claim 1, wherein the content search of the firehose filter is configured to perform keyword or phrase searches.

5. The system of claim 1, further including a triage process.

6. The system of claim 5, wherein the triage process includes one or more of a triage queue, a triage database, and an action database.

7. The system of claim 1, further including a clustering filter configured to filter out non-relevant posts.

8. The system of claim 1, wherein the single post filter includes one or more of a single post feature extractor, a single post classifier, and a single post classifier learning algorithm.

9. The system of claim 1, wherein the contextual filter includes one or more of a contextual data harvester, a contextual feature extractor, a contextual classifier, and a contextual classifier learning algorithm.

10. The system of claim 1, wherein the target population filter includes one or more of a non-relational user classifier learning algorithm, a non-relational user classifier, and a non-relational user feature extractor.

11. The system of claim 1, further including a candidate pool update feature including one or more of a new candidate algorithm, a relational user feature extractor, and a relational user classifier learning algorithm.

12. A software method, having a plurality of filters, for social media account monitoring, comprising:
executing a sampling scheduler configured to prioritize sampling based on capacity for processing posts, wherein the sampling scheduler directs post data to input at least a plurality of the plurality of filters, including processed post data from a previous filter, with the sampling scheduler configured to selectively provide instructions to skip one or more of the plurality of filters based on target rates of posts to sample,
selectively executing one or more firehose filters configured to perform a content search all social media posts from one or more sources to determine a firehose post data output, including social media post data, to send to the sampling scheduler;
selectively executing a single post filter configured to read post data from a single post input to process one or more features from a single social media post object to determine relevant social media posts to include in a single post data output to send to the sampling scheduler;
selectively executing a contextual filter configured to read post data from a contextual input to gather and process additional data beyond data processed by the single post filter to augment classification and to include in a contextual post data output to send to the sampling scheduler; and
selectively executing a target population filter configured to read post data from a population input to determine if one or more users are to be identified for a target social media user population such that one or more identified users with one or more probability scores are stored in a target candidate pool with other identified users to identify user relevance for additional monitoring or review.

13. The method of claim 12, wherein the target population filter is executed prior to execution of the single post filter.

14. The method of claim 12, wherein the target population filter is executed after the execution of the contextual filter.

15. The method of claim 12, wherein the content search of the firehose filter is configured to perform keyword or phrase searches.

16. The method of claim 12, further including a triage process having one or more of a triage queue, a triage database, and an action database.

17. The method of claim 12, wherein the single post filter includes one or more of a single post feature extractor, a single post classifier, and a single post classifier learning algorithm.

18. The method of claim 12, wherein the contextual filter includes one or more of a contextual data harvester, a contextual feature extractor, a contextual classifier, and a contextual classifier learning algorithm.

19. The method of claim 12, further including executing a clustering filter configured to filter out non-relevant posts.

20. A non-transitory computer readable medium having stored thereon program code having a plurality of filters and configured for social media account monitoring, comprising:
a sampling scheduler configured to prioritize sampling based on capacity for processing posts, wherein the sampling scheduler directs post data to input at least a plurality of the plurality of filters, including processed post data from a previous filter, with the sampling scheduler configured to selectively provide instructions to skip one or more of the plurality of filters based on target rates of posts to sample,
the plurality of filters including:
one or more firehose filters configured to perform a content search of all social media posts from one or more sources to determine a firehose post data output, including social media post data, to send to the sampling scheduler;
a single post filter configured to read post data from a single post input to process one or more features from a single social media post object to determine relevant social media posts to include in a single post data output to send to the sampling scheduler;
a contextual filter configured to read post data from a contextual input to gather and process additional data beyond data processed by the single post filter to augment classification and to include in a contextual post data output to send to the sampling scheduler; and
a target population filter configured to read post data from a population input to determine if one or more users are to be identified for a target social media user population such that one or more identified users with one or more probability scores are stored in a target candidate pool with other identified users to identify user relevance for additional monitoring or review.

* * * * *